US006793390B2

(12) United States Patent
Wang et al.

(10) Patent No.: US 6,793,390 B2
(45) Date of Patent: Sep. 21, 2004

(54) METHOD FOR AUTOMATIC ARRANGEMENT DETERMINATION OF PARTIAL RADIATION IMAGES FOR RECONSTRUCTING A STITCHED FULL IMAGE

(75) Inventors: Xiaohui Wang, Pittsford, NY (US); David H. Foos, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 167 days.

(21) Appl. No.: 10/268,452

(22) Filed: Oct. 10, 2002

(65) Prior Publication Data

US 2004/0071269 A1 Apr. 15, 2004

(51) Int. Cl.[7] .............................................. G03B 42/02
(52) U.S. Cl. ........................................ 378/174; 378/62
(58) Field of Search .......................... 378/62, 167, 174

(56) References Cited

U.S. PATENT DOCUMENTS

| | | | | |
|---|---|---|---|---|
| 4,613,983 A | | 9/1986 | Yedid et al. ................. 378/982 |
| 5,528,043 A | * | 6/1996 | Spivey et al. .......... 250/370.09 |
| 5,986,279 A | | 11/1999 | Dewaele ...................... 250/982 |
| 6,269,177 B1 | | 7/2001 | Dewaele et al. ............. 382/131 |
| 6,273,606 B1 | | 8/2001 | Dewaele et al. ............. 378/174 |
| 6,459,094 B1 | * | 10/2002 | Wang et al. ................. 250/584 |
| 2002/0109113 A1 | * | 8/2002 | Wang et al. ................. 250/584 |
| 2003/0048938 A1 | * | 3/2003 | Wang et al. ................. 382/132 |

FOREIGN PATENT DOCUMENTS

| | | | | |
|---|---|---|---|---|
| EP | 0866342 A1 | 9/1998 | | |
| EP | 0919856 A1 | 6/1999 | | |
| EP | 0919858 A1 | 6/1999 | | |
| EP | 1231484 A2 | * | 8/2002 | ............ G01T/1/29 |
| EP | 1291677 A2 | * | 3/2003 | ............ G01T/1/29 |
| JP | 2000232976 A | 8/2000 | | |
| JP | 2000250153 A | 9/2000 | | |
| JP | 2000258861 A | 9/2000 | | |
| JP | 2000267210 A | 9/2000 | | |
| JP | 20002419250 A | 9/2000 | | |

OTHER PUBLICATIONS

A new fully automatic method for CR image composition by white band detection and consistency rechecking, SPIE Medical Imaging, 2001, vol. 4322, pp 1570–1573, Guo–Qing Wei et al.

* cited by examiner

*Primary Examiner*—David V Bruce
(74) *Attorney, Agent, or Firm*—William F. Noval

(57) ABSTRACT

A method for automatic arrangement determination of partial radiation images for reconstructing a stitched full image. At least two radiation sub-images of an elongated object are acquired and converted to digital images. A hypothesis list is constructed and overlap regions for consecutive sub-images pair in each hypothesis are detected. A plurality of different measurements are conducted on consecutive sub-image pair of each hypothesis. The correlation function is calculated to find the function maximum and the horizontal displacement between the sub-image pair. The magnitude of the horizontal displacement is checked and an overall figure-of-merit is established. The hypothesis of maximum figure-of-merit for best candidate is selected. The sub-images are processed based on selected hypothesis for stitching to produce an output image.

17 Claims, 10 Drawing Sheets

FIG. 8

METHOD FOR AUTOMATIC ARRANGEMENT DETERMINATION OF PARTIAL RADIATION IMAGES FOR RECONSTRUCTING A STITCHED FULL IMAGE

FIELD OF THE INVENTION

This invention relates in general to digital radiography, and in particular to the imaging of a long human body part, such as the spine or legs, using a storage phosphor-based computed radiography system.

BACKGROUND OF THE INVENTION

When a long segment of the human body is imaged using the conventional screen-film technique, special cassettes and films of extended length are used, such as 14"×36" and 14"×51". As medical institutions are migrating from analog screen-film systems to digital modalities, such as computed radiography (CR), these types of exams impose a significant challenge. This is because the size of digital detector is limited. For example, the largest CR storage phosphor cassette from several major CR vendors is limited to 14"×17", which can only image a portion of the long body part at a time.

Several methods have been proposed to extend the CR imaging coverage by stacking several existing standard CR cassettes. European Patent Application 0919856A1 (also U.S. Pat. No. 6,273,606B1) discloses a way of overlapping several storage phosphor cassettes 101 adjacently. The cassettes can be in the alternating (FIG. 1A), staircase-wise (FIG. 1B), or oblique (FIG. 1C) arrangement. During the x-ray exposure, all the partially overlapping cassettes are exposed simultaneously, therefore each storage phosphor screen 102 that resides inside the corresponding cassette records a part of the image of the long body part. Similar approach is disclosed by Japanese Patent Application 2000250153A. European Patent Application 0866342A1 (also U.S. Pat. No. 5,986,279A) presents a method that is based on partially overlapping a plurality of storage phosphor screens for extended imaging coverage. The screens 102 can also be configured in the alternating (FIG. 1D), staircase-wise (FIG. 1E), or oblique (FIG. 1F) overlapping arrangement in a single elongated cassette 103. Similar approaches are proposed in Japanese Patent Application 2000267210A and 2000241920A. Further, cassettes and screens can be used together in alternating arrangement as shown in FIG. 1G, the cassettes 101 and storage phosphor screens 102 are placed in a partially overlapping and alternating arrangement with the screens 102 always positioned in front of the cassettes 101. This method eliminates the cassette shadow from the acquired images, and reduces the number of storage phosphor screens that need to be removed out of and to be replaced back into cassettes.

Because the phosphor screens are the fundamental imaging recording devices, no matter whether the screens are packaged within the individual cassette or not, the term "storage phosphor screen", "phosphor screen", or "screen" is used hereinafter to represent either the phosphor screen itself or the phosphor screen that is conveyed inside a cassette. Therefore the different scenarios in FIG. 1 are reduced to alternating, staircase-wise, and oblique arrangements of overlapping phosphor screens, with the exception that the distance between the screen planes can vary for each scenario depending on if the screen(s) is conveyed inside the cassette or not.

A schematic view of how a patient radiographic image is acquired is shown in FIG. 2. The patient (element 203) is positioned between the x-ray source (element 201) and a plurality of screens (element 205). Any of the screen arrangement methods shown in FIGS. 1A–1G can be used for imaging. An optional anti-scatter grid (element 204) can be placed between the patient and the screens. The grid can be either a stationary type or reciprocating type. During x-ray exposure, the x-rays can be collimated to minimize the radiation to the nondiagnostically relevant patient anatomy. After the x-ray generator is fired and the cassette is exposed, the image of the patient is recorded by the plurality of screens as latent radiographic signals. Each screen captures only a portion of the image of the patient. The screens are fed into a CR reader and the latent radiographic signals are converted to electronic images. The electronic image acquired from an individual screen will be referred to as a sub-image.

The sub-images acquired by the individual storage phosphor screens must be stitched together to create a composite full image. Information about the spatial order, orientation, and overlap arrangement of the phosphor screens used during x-ray exposure is required in order to stitch together the composite image. After x-ray exposure, the phosphor screens may be scanned in an arbitrary order in the CR reader. It is therefore necessary to rearrange the sequence of the scanned sub-images into the order corresponding to the physical setup used for image acquisition. It is also required that the overlap arrangement between consecutive screens be known exactly. For example, screens can overlap either on the top or on the bottom in cases of staircase-wise and oblique screen arrangements, and in the case of alternating screen arrangement, screens closer to the x-ray source overlap differently from those further away. A screen may be equivalently positioned for image capture in the landscape (horizontal) orientation with either of the two long dimensions facing up. Consequently, a scanned sub-image may be rotated 180° from an adjacent sub-image. Detection of sub-image rotation is therefore necessary.

U.S. Pat. Nos. 4,613,983 and 5,833,607 each disclose methods to reconstruct a composite radiographic image from a set of sub-images. The former method is predicated on all sub-images being sequentially acquired and scanned in a predetermined spatial position and orientation. The latter method relies on a hardware position sensor to determine the relative position of each sub-image during acquisition. Neither of these two methods can be applied to the situation when the scanned sub-image sequence does not match the sequence used during acquisition. European Patent Application 0919858A1 (also U.S. Pat. No. 6,269,177B1) proposes a stitching method that utilizes a pattern of reference markers for the alignment of sub-images. However, this patent does not teach how the sub-images are ordered and requires that the sub-images are properly oriented prior to the stitching operation. Another stitching method was proposed by Wei et al. ("A new fully automatic method for CR image composition by white band detection and consistency rechecking," Guo-Qing Wei, et al., Proceedings of SPIE Medical Imaging, 2001, vol. 4322, pp 1570–1573), to automatically stitch sub-images read from phosphor sheets in staircase-wise arrangement. However, this method assumes the sub-images are already pair-wise sequentially arranged before stitching.

Japanese Patent Application 2000258861A discloses a method that depends upon two different identification labels attached on every phosphor screen as auxiliary information for determining the orientation and location of the corresponding screen. Japanese Patent Application 2000232976A further teaches how the auxiliary information can be used in the stitching process. However, it is desirable not to use auxiliary information at all because doing so usually means either the standard cassette needs to be modified or the standard phosphor screen IDs need to be replaced, both of which may cause the cassette or screen incompatible for other general purposes.

It is therefore desirable to develop an automatic method to determine the spatial order, orientation, and overlap arrangement of the phosphor screens used in the x-ray exposure directly based on the acquired sub-images.

SUMMARY OF THE INVENTION

According to the present invention, there is provided a solution to the problems discussed above.

According to a feature of the present invention, there is provided a method of a method for automatic arrangement determination of partial radiation images for reconstructing a stitched full image comprising: acquiring at least two radiation sub-images of an elongated object by means of corresponding overlapped radiation recording media; converting said recorded sub-images to digital images and storing them; constructing a hypothesis list that includes all possible yet unique arrangements of sub-image order, orientation and overlap; detecting overlap regions for each consecutive sub-images pair in each hypothesis; conducting a plurality of different measurements on every consecutive sub-image pair of each hypothesis and deleting the hypothesis from the list if any measurement result is out of range; calculating the correlation function of the overlap regions for each consecutive sub-image pair in each hypothesis left in said hypothesis list and finding the function maximum and the horizontal displacement between the sub-image pair; checking the magnitude of the horizontal displacement between each consecutive sub-image pair and rejecting the consecutive sub-image pair and rejecting the hypothesis form the hypothesis list if the magnitude is out of range; establishing an overall figure-of-merit for each hypothesis left in the hypothesis list based on the sum of the maximum of the correlation functions; selecting the hypothesis of maximum figure-of-merit for best candidate; and processing the sub-images based on selected hypothesis for stitching to produce an output image consisting of the stitched sub-images.

ADVANTAGEOUS EFFECT OF THE INVENTION

The invention has the following advantages:
1. This invention allows automatic determination of the spatial order, orientation, and overlap arrangement of the phosphor screens used in the x-ray exposure directly based on the acquired sub-images.
2. The method allows phosphor screens to overlap arbitrarily, to be positioned with a 180° variability, and to be scanned in the CR reader in any order.
3. When the invention is combined with an automatic image stitching method, the entire process of producing a composite image from a set of sub-images can be made fully automatic.

BRIEF DESCRIPTION OF THE DRAWINGS

FIG. 8 lists all the hypotheses that include different spatial order, orientation, and overlap arrangements of the sub-images when three screens are used in alternating arrangement.

DETAILED DESCRIPTION OF THE INVENTION

In general, the present invention relates to the radiographic imaging of an elongated object such as the full spine, e.g., for diagnosing scoliosis, or full leg of a human subject.

Figure 2:
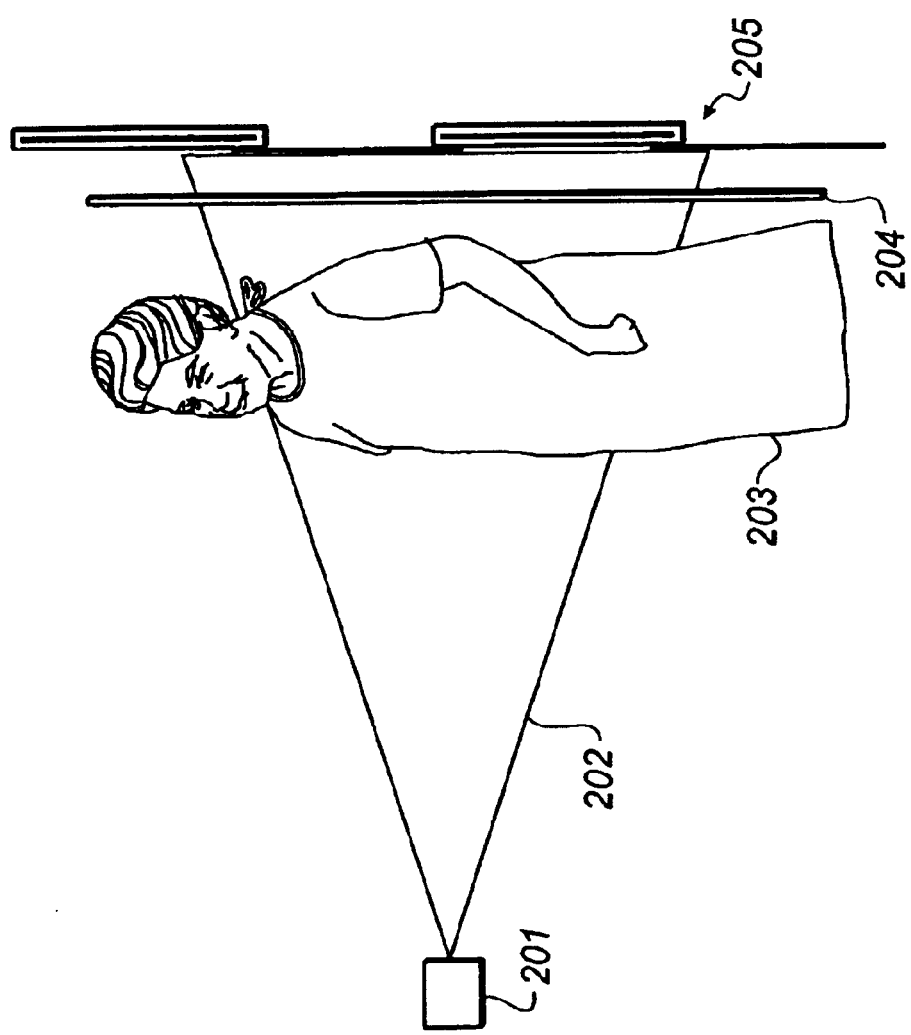
FIG. 2 is a diagrammatic view showing a method for image acquisition using the alternating phosphor screen/cassette configuration shown in FIG. 1G as an example. Any of the other configurations shown in FIG. 1 can also be used for acquiring the images.
Figure 3A:
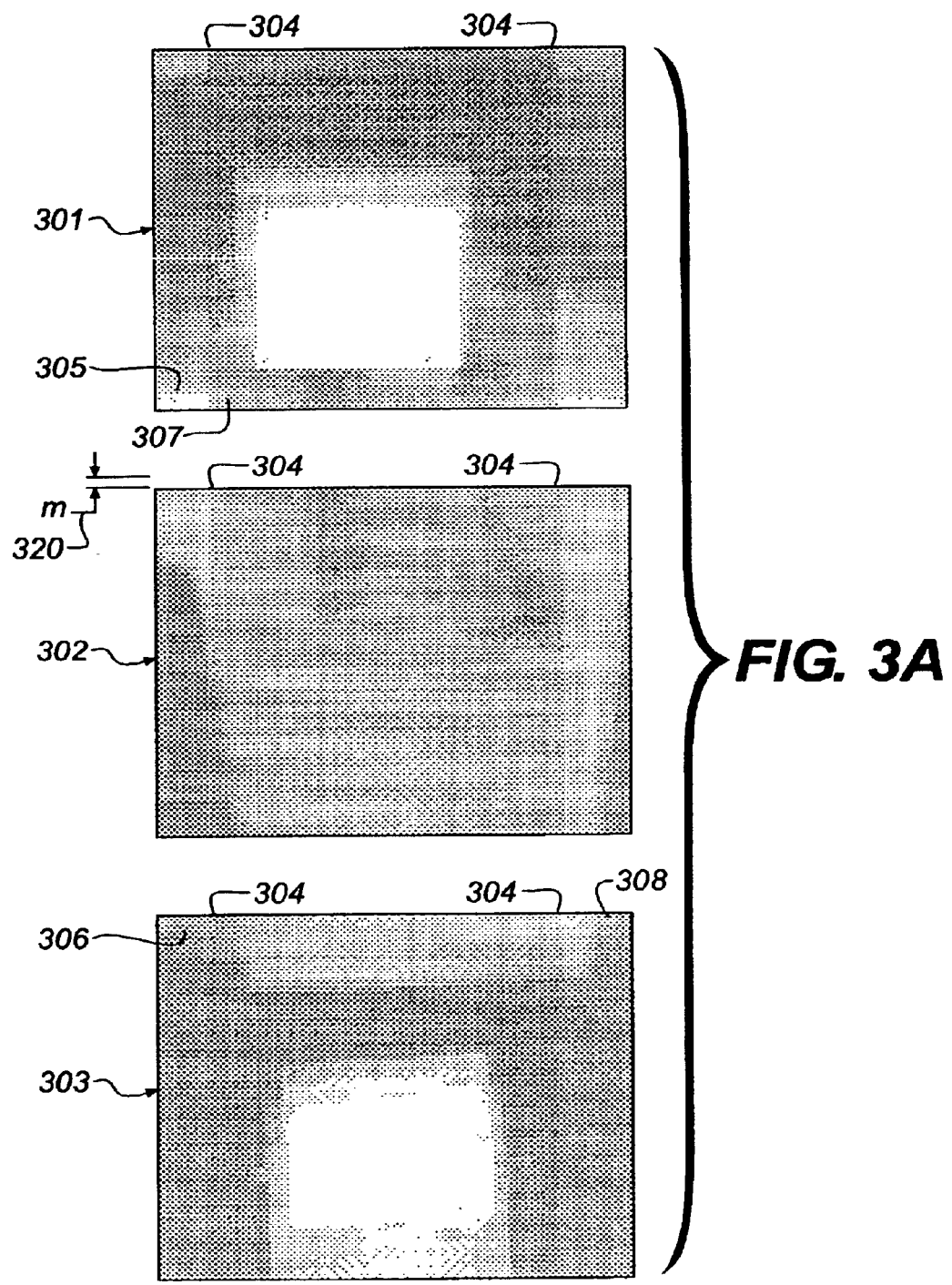
FIG. 3A is a diagrammatic view showing three sub-images acquired using the configuration shown in FIG. 1G. The middle image 302 is recorded on a storage phosphor screen (either the screen itself or the screen within a cassette) that is placed closer to the x-ray source. The top image 301 and the bottom image 303 are recorded on two storage phosphor screens (either the screen itself or the screen within a cassette) that are placed behind the middle screen. The shadow of the middle screen top edge is recorded in image 301, and the shadow of the bottom-edge is recorded in image 303.

FIG. 3A shows an example for the case where three storage phosphor screens are exposed. The images are acquired using the radiation exposure method of FIG. 2 and the phosphor screen configuration of FIG. 1G. The two phosphor screens that capture the first image (element 301) and the third image (element 303) are placed behind the screen that captures the second image (element 302).

Because the first screen 301 and the second screen 302 partially overlap, and the second screen 302 is not totally opaque to the incident x-rays, the first screen 301 still captures the image of the patient in the screen overlap region (element 307). However, the signal-to-noise ratio of the image captured on the first screen 301 in the overlap region will be relatively lower because of the x-ray attenuation caused by the second screen 302 The top edge of the second screen 302 also imposes a distinct shadow in the first image, as indicated by element 305. Similarly, the bottom edge of the second screen 302 imposes a shadow in the third image, as indicated by element 306 in screen 303. In all three images, the boundaries between the collimated and non-collimated exposure regions are indicated by element 304.

As explained above the exposed storage phosphor screens are read out in a CR reader to produce electronic images which are digitized, the images formed of a matrix of pixels. According to the invention, the storage phosphor screens are overscanned beyond the top and bottom edges of the exposed image region of the storage phosphor screen.

The relationship between any two adjacent screens is equivalent for the screen configurations shown in FIGS. 1A–1G. The screens partially overlap and one screen is positioned closer to the x-ray source. The term "front screen" will be used to refer to the screen that is positioned closer to the x-ray source, and the term "front image" will be used to refer to the image captured with the front screen. Similarly, the terms "back screen" and "back image" are used to refer to the screen that is positioned further from the x-ray source and "back image" will refer to the image captured with the "back screen". When a group of N adjacently overlapping screens are used for an x-ray exposure (N>=2), the screens can be divided into N-1 screen pairs, each of which consists of two adjacent screens—one front screen and one back screen. By this definition, one screen can be the front screen in one "screen pair", and can also be the back or the front screen in the next screen pair.

Figure 4B:
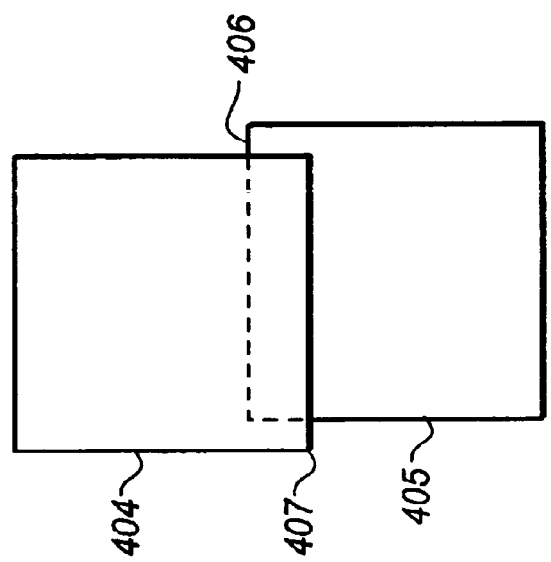
FIGS. 4A and 4B are diagrammatic views illustrating the definitions of the front screen, back screen, front screen overlap edge, and back screen overlap edge.
Figure 4A:
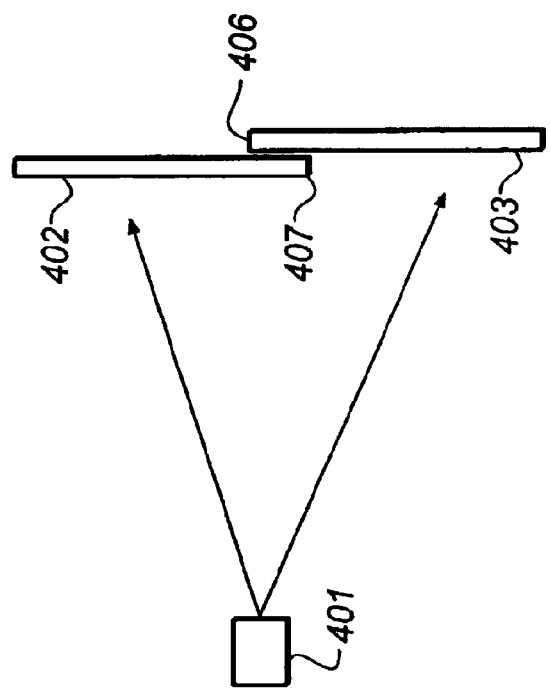

FIGS. 4A and 4B illustrate additional terminology useful in explaining the present invention where the back and front overlap edges of screens 403 and 402 are indicated by elements 406 and 407 respectively. Device 401 is a source of x-rays.

In the following description of the invention, the term "vertical" is used to mean the direction in which the phosphor screens are stacked and the term "horizontal" is used to mean the direction perpendicular to the "vertical". It will be understood that the screens can be oriented in any direction during x-ray exposure.

Figure 5:
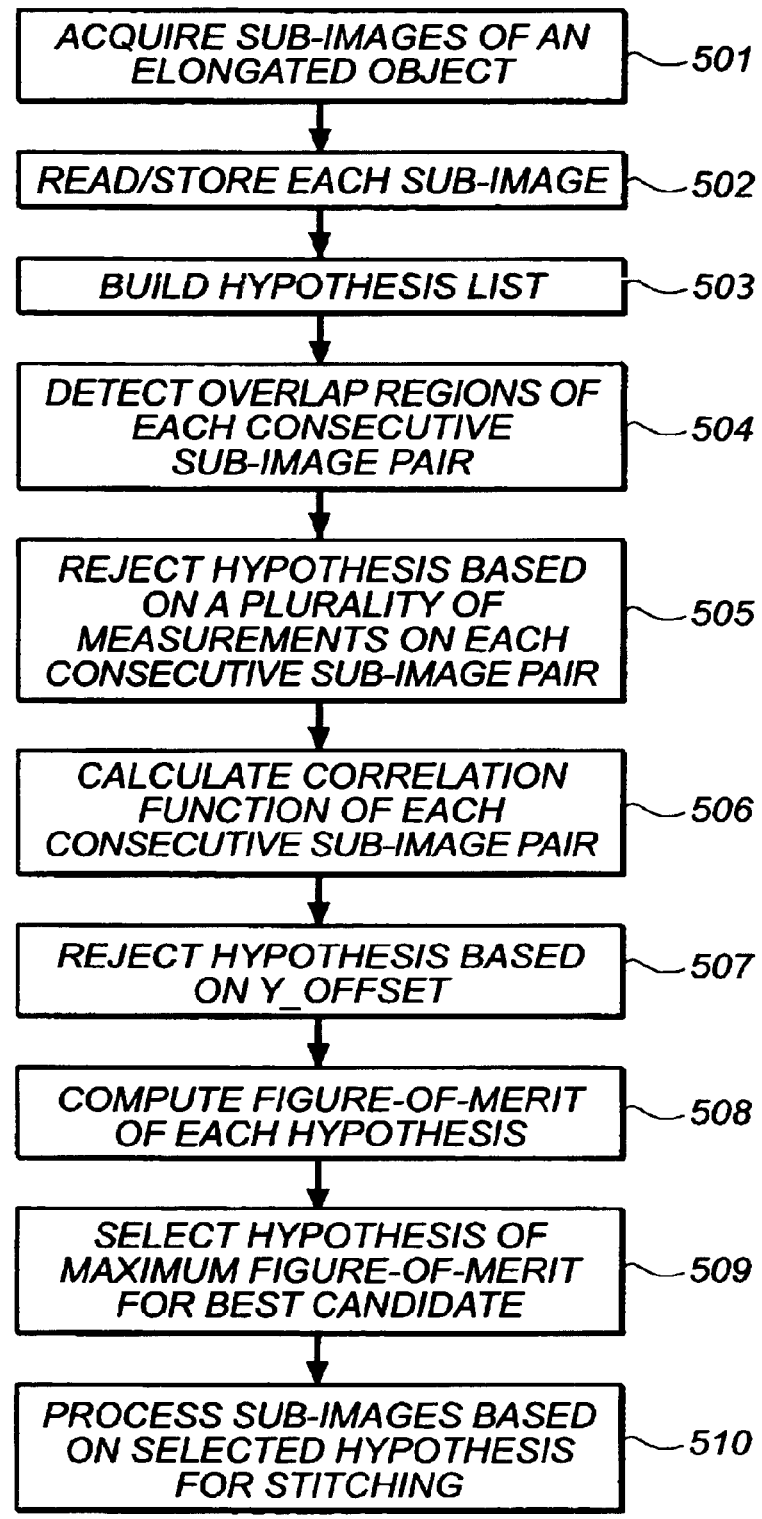
FIG. 5 is a flow diagram showing an embodiment of the method of the present invention.

Referring now to FIG. 5 there is shown an embodiment of the present invention for the automatic determination of the spatial order, orientation, and overlap arrangement of the phosphor screens in an x-ray exposure directly from the acquired sub-images. The method includes: acquiring sub-images of an elongated object (box 501); reading and storing each sub-image (box 502); constructing a hypothesis list that includes all possible yet unique arrangements of sub-image order, orientation, and overlap (box 503); detecting regions for each consecutive sub-image pair in each hypothesis (box 504); conducting a plurality of measurements on every consecutive sub-image pair of each hypothesis and deleting the hypothesis from the list (box 505) if any measurement result is out of range, such as the size of the overlap region, the average pixel intensity difference between the overlap regions in the front and back images, the overall transition magnitude of the shadow of front screen overlap edge in the back image, or the overall transition magnitude of the dominant horizontal line in the front image, etc.; calculating the correlation function of the overlap regions for each consecutive sub-image pair in each hypothesis left in the list and, finding the function maximum and the horizontal displacement between the sub-image pair (506); checking the magnitude of the horizontal displacement between each consecutive sub-image pair and rejecting the hypothesis from the list if the magnitude is out of range (507), establishing an overall figure-of-merit for each hypothesis left in the list based on the sum of the maximum of the correlation function(s) (box 508); selecting the hypothesis of maximum figure-of-merit for best candidate (box 509); and processing sub-images based on selected hypothesis for stitching to produce an output image consisting of the stitched sub-images (box 510). The steps of boxes 505 and 507 work on the local level of a consecutive sub-image pair and use measurements with loosely defined thresholds to reject those false hypothesis. The step of box 508 works on the overall level of a hypothesis, and the step of box 509 work on the global level to identify the most likely candidate based on figure-of-merit. By making the algorithm work on different levels of analysis, the computational efficiency can be significantly improved while still satisfying the requirement on detection robustness.

Figure 1:
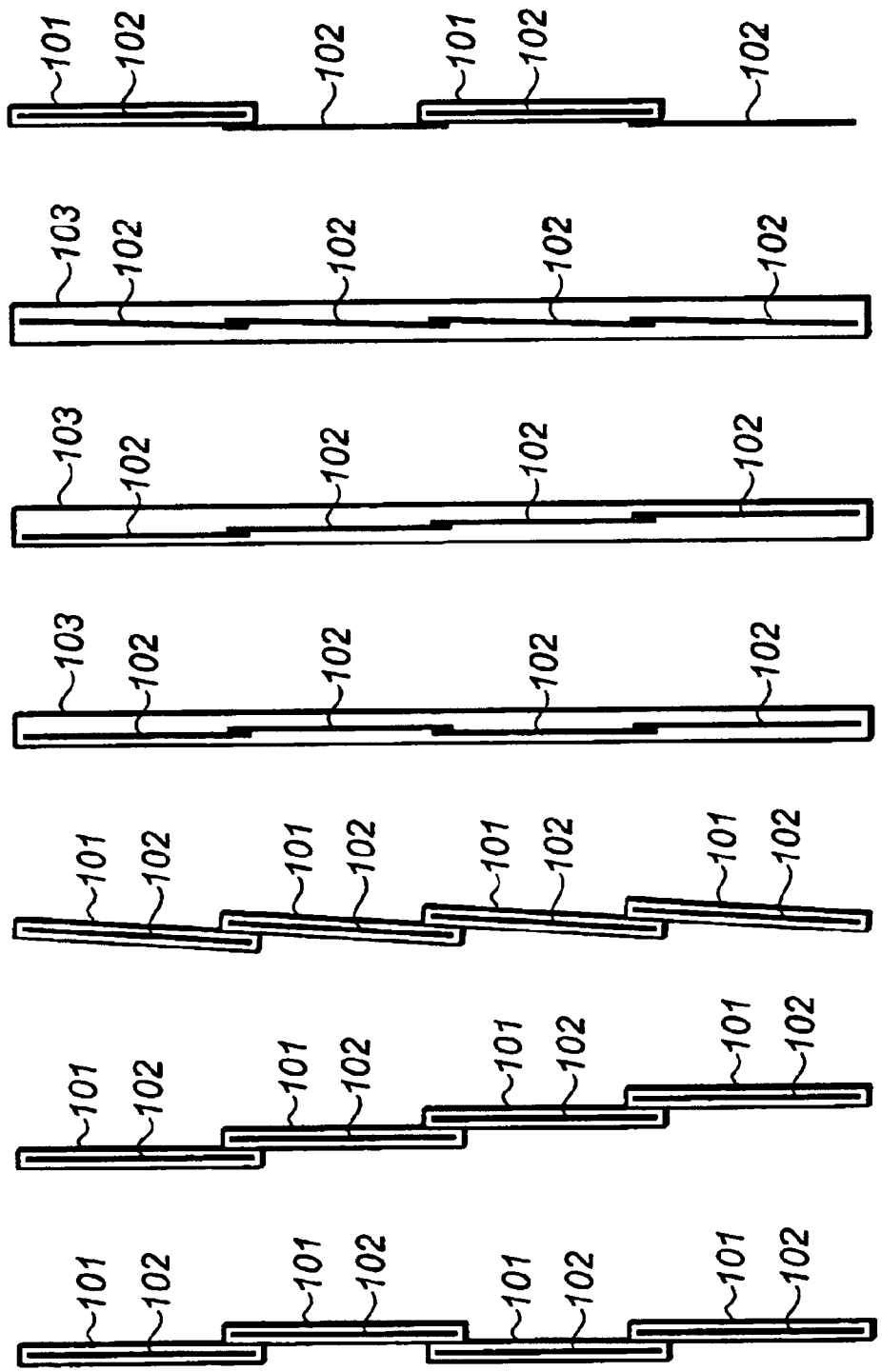
FIGS. 1A–1C are diagrammatic views showing a plurality of storage phosphor cassettes, with each cassette containing one storage phosphor screen, arranged in alternating, staircase-wise, and oblique positions, respectively. The storage phosphor screens are represented as solid vertical lines inside the cassettes.
FIGS. 1D–1F are diagrammatic views showing a plurality of storage phosphor screens arranged in alternating, staircase-wise, and oblique positions, respectively. The screens can be contained within a single, extended length cassette.
FIG. 1G is a diagrammatic view showing a configuration consisting of a set of storage phosphor screens/cassettes that are placed in an alternating arrangement with the screens placed in front of the cassettes (closer to x-ray source).

The detailed embodiment of this invention is described based on the screen arrangement in FIG. 1G. It is understood that the spirit of this work can be applied to alternating, staircase-wise, oblique, or any arbitrary overlapping arrangements.

The method of the invention is carried out by a CR reader which converts the screen images into digital sub-images, and image processor, such as a digital computer or microprocessor for carrying out said storing through processing to produce an output image which can be displayed on a monitor or printed out as landscapes.

Figure 8:
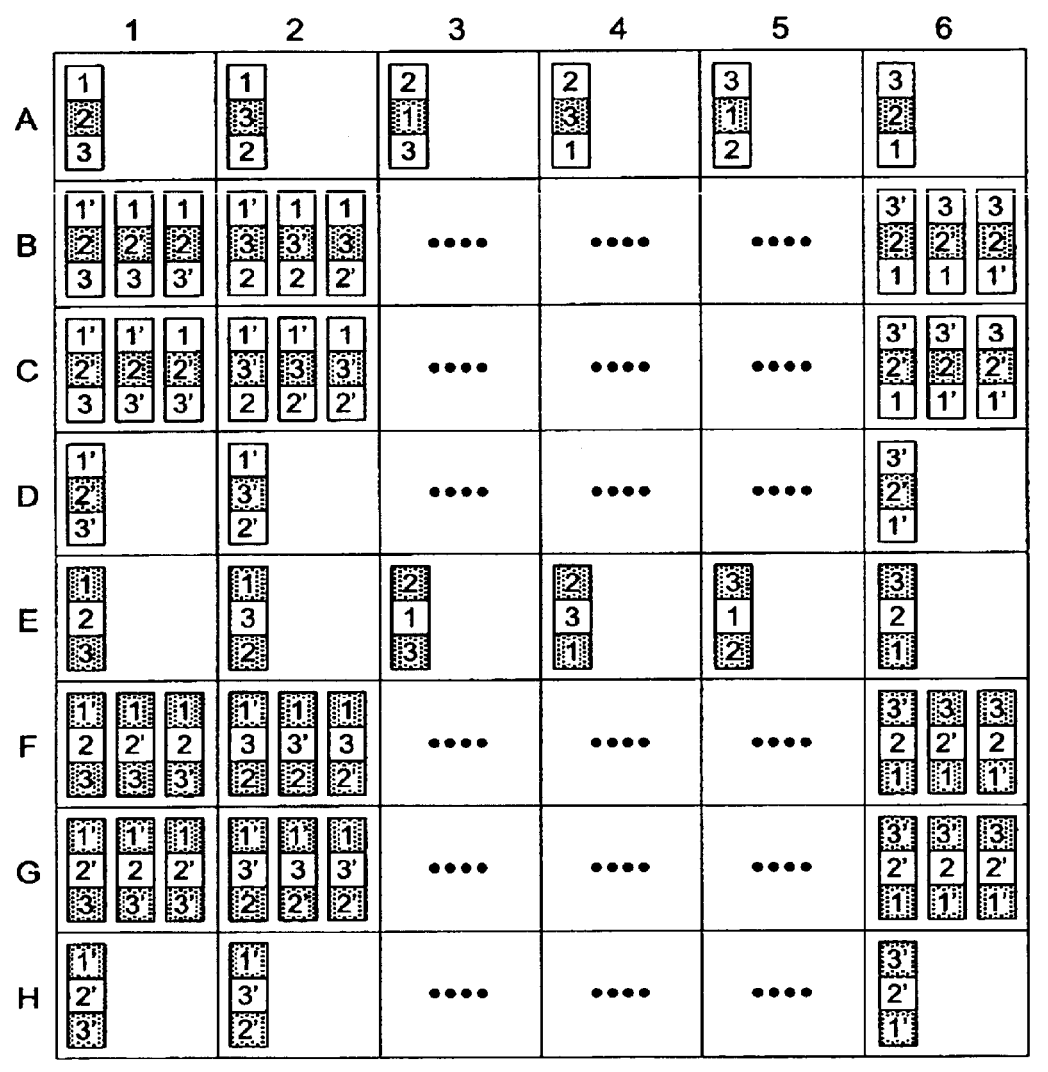

The initial step of the invention is to construct a hypothesis list that includes all possible yet unique arrangements of sub-image order, orientation, and overlap. For example, FIG. 8 shows in rows A–H and columns 1–6 all the possible hypotheses of sub-image arrangements for three screens of alternating overlapping screens. In each hypothesis diagram, the squares 1, 2, 3 represent individual sub-images and the numbers inside are uniquely assigned when the phosphor screens are scanned by the CR reader. The open squares mean that the corresponding sub-images are acquired from the phosphor screens closer to the x-ray source, and the shaded squares mean that the sub-images are acquired from screens that are farther away from the x-ray source. When a sub-image is rotated, the corresponding number is commented by the symbol "'". For example, "2'" means sub-image 2 is rotated by 180°.

More specifically, rows A, B, C and D show the various sub-image arrangements where the top and bottom sub-images are closer to the x-ray source and the central sub-image is farther away from the x-ray source. Rows E, F, G, and H show the various sub-image arrangements where the top and bottom sub-images are farther away from the x-ray source and the central sub-images is nearer the x-ray source. Row A, Col. 1 through Row A, Col. 6 respectively show sub-image arrangements from top to bottom as follows: 1, 2, 3; 1, 3, 2; 2, 1, 3; 2, 3, 1; 3, 1, 2; and 3, 2, 1. In rows B and C, three arrangements of sub-images are shown in each box. Row B, Col. 1, shows sub-image arrangements $1^1$, 2, 3; 1, $2^1$, 3; 1, 2, $3^1$ and Row B, Col. 2, shows sub-image arrangements $1^1$, 3, 2; 1, $3^1$, 2; 1, 3, $2^1$. Similarly, Row C, Col. 1, shows sub-image arrangements $1^1$, $2^1$, 3; $1^1$, 2, $3^1$, 1, $2^1$, $3^1$; and Row C, Col. 2, shows sub-image arrangements $1^1$, $3^1$, 2; $1^1$, 3, $2^1$; 1, $3^1$, $2^1$. Proceeding further, single sub-image arrangements are shown in the boxes in Rows D, E, and H, whereas three sub-image arrangements are shown in the boxes in Rows F and H. The sub-image arrangements for the boxes of Rows B, Col. 3, 4 and 5; Row C, Col. 3, 4 and 5; Row D, Col. 3, 4 and 5; Row F, Col. 2, 4 and 5; Row G, Col. 3, 4 and 5; and Row H, Col. 3, 4 and 5; and Row H, Col. 3, 4 and 5 are not shown but are easily derivable from the sub-image arrangements shown.

Figure 3B:
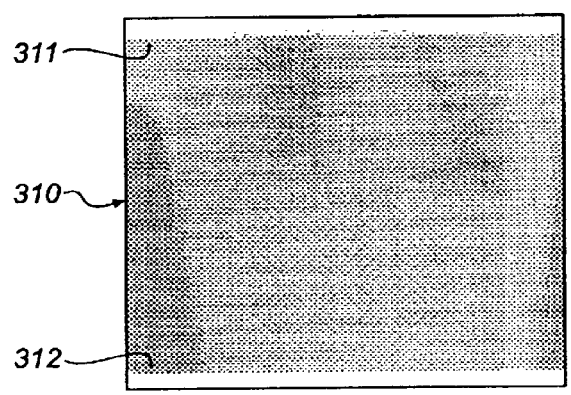
FIG. 3B is a diagrammatic view showing a modification of the middle image of FIG. 3A.

The next step is to detect the overlap regions for each consecutive sub-image pair in each hypothesis (FIG. 5, box 504). This is a critical step because a number of analyses are conducted within the overlap region. The overlap region in the back image has a relatively lower signal magnitude and it is simply separated from the rest of image by the shadow of the front screen overlap edge. If the front screen overlap edge is known in the front image, it can be matched with its shadow in the back image and the overlap region in the front image can be determined based on the size of the overlap region in the back image. One way to deterministically locate the front screen overlap edge in the front image is to make the CR reader over-scan the front phosphor screen beyond the overlap edge, which is usually not available or guaranteed in a conventional CR reader. Using the modified image (element 310) in FIG. 3B as an example, the top and bottom edges of the phosphor screen are over-scanned, therefore both edges are completely visible (elements 311 and 312) in the sub-image pixel matrix.

The following description for detecting the overlap regions of a particular sub-image pair assumes that the CR reader is capable of over-scanning both the top and bottom edges of all the phosphor screens. It is understood that many variations can be derived based on the spirit of the description.

Figure 6:
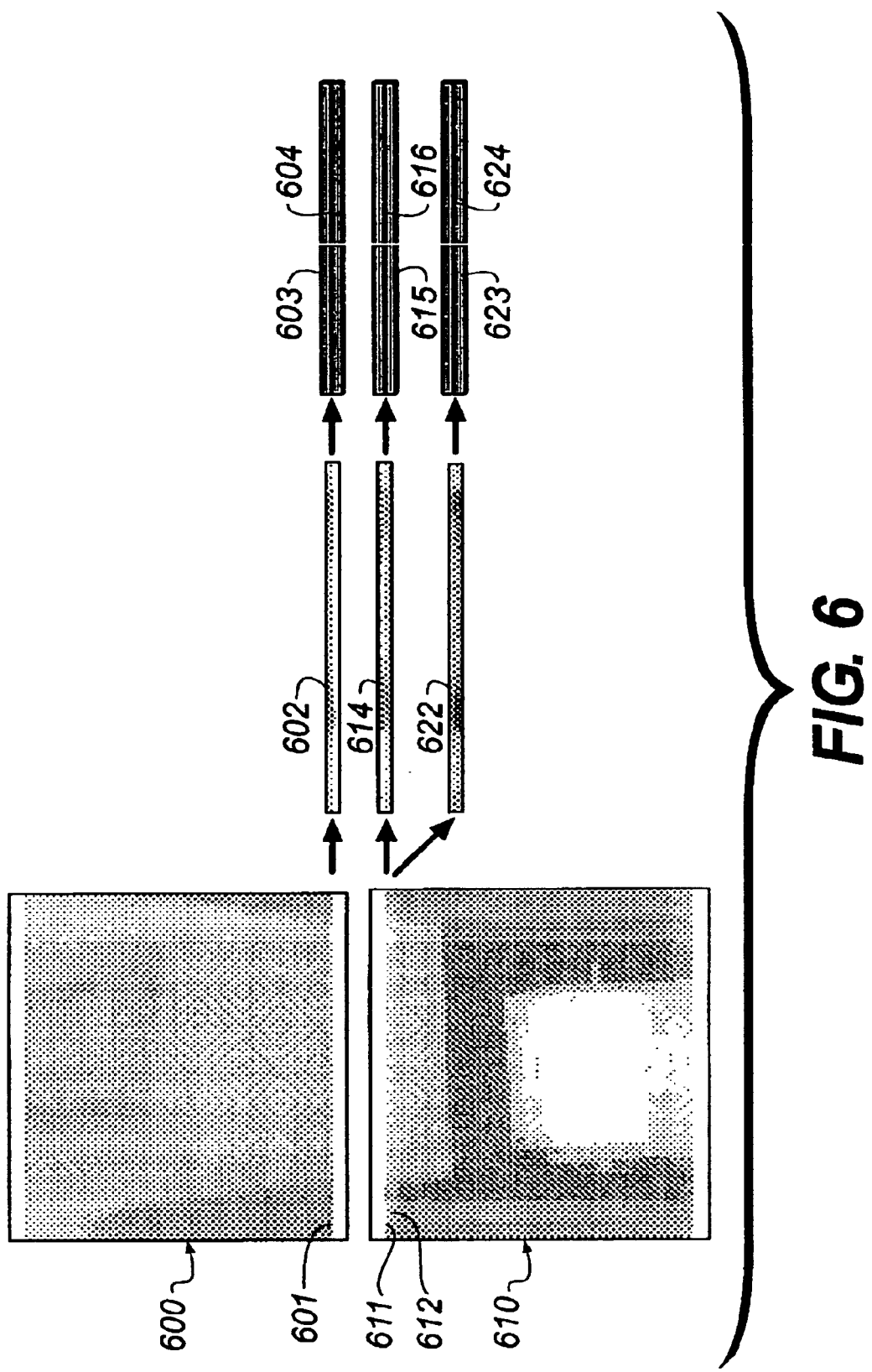
FIG. 6 is a diagrammatic view illustrating the major image processing steps that are used to automatically find the locations and orientations of the screen overlap edges in both the front and the back images, and for finding the location and orientation of the shadow of the front screen overlap edge in the back image.

The screen overlap edges are first located correspondingly from the front and back images, followed by detecting the shadow of the front screen overlap edge in the back image. These steps are illustrated in FIG. 6. The pixel values in the image region that is beyond the screen overlap edge reflect the baseline noise level of the CR reader. This is because there is no signal contribution from the phosphor screen. Consequently, the pixel values in these regions are relatively low in comparison to those in the exposed image regions, therefore there is an abrupt pixel value decrement/discontinuity across the screen overlap edge in the image. This pixel value discontinuity is used to detect the location and orientation of the screen overlap edges, which can be accomplished in many ways. In the preferred embodiment of the present invention, the detection is carried out by (1) computing all of the significant edge transition pixels in the proximity of the screen overlap edge, and (2) performing line delineation of the candidate transition pixels of the screen overlap edge.

Using the front image as an example, FIG. 6 describes the preferred embodiment of the detection process. First, a narrow band 602 is extracted from the end of the front image 600. Depending on how the phosphor screen is being scanned in the CR reader, the orientation of the screen ending edge 601 can have a variation of several degrees in the acquired image from one scan to the next scan. Therefore, the size of the narrow band must be large enough such that the entire screen ending edge can be reliably extracted. For an image that has a width of 2,048 pixels, the size of the narrow band should be approximately 200×2,048 pixels.

Second, the one-dimensional derivative of the image is computed in the vertical direction. A one-dimensional derivative operator, such as $[-1,0,1]$, $[-1,0,0,0,1]$, or $[-1,0,0,0,0,]$ etc., is preferred because the pixel value discontinuity only occurs across the edge direction, which is always nearly horizontal, and because of the computational efficiency advantages. A predefined threshold is used to select only those candidate edge transition pixels that are of greater magnitude and of falling slope. Element 603 shows the results from this step. It has been found that applying a two-dimensional low-pass filtering to the narrow band helps to improve the detection accuracy. In a preferred embodiment of this invention, the narrow band is low-pass filtered.

Third, a linear function is fitted to the candidate edge pixels and the best fitting parameters are obtained when the least square error is reached. Element 604 shows the fitted linear function overlaid on top of the edge transition pixels. Similarly, this process is conducted for the back image 610, except rising edge transition pixels are searched instead inside a narrow band 614 at the beginning of the back image.

Once the screen overlap edge is successfully found in the front image, it is compared with its shadow in the back image for image registration. To locate the shadow of the front screen overlap edge in the back image, an approach similar to the method used in detecting the screen overlap edge is used. This is possible because the pixel values in the back image also undergo a strong signal intensity decrement in the screen overlap region due to the high attenuation of the incident x-rays by the front screen. The location of the narrow band for detecting the shadow of the front image overlap edge can be calculated based on the approximate overlap size between the phosphor screens, which should be a priori. The size of the narrow band can be enlarged in order to broaden the searching range.

It is more computational efficient to detect the screen overlap edges and the candidate shadows of the front screen overlap edge at the very beginning of the whole process of this invention. Because every sub-image has a chance to be treated as a back image in the hypothesis list with the overlap either at the top or the bottom, the detection of the screen overlap edge and the candidate shadow of the front screen overlap edge can be performed once for all at the top and at the bottom of each image. The results are saved and used later. The term "candidate shadow of front screen overlap edge" is used because the shadow does not exist in practice for the front image in a consecutive sub-image pair, in which case the identified line is simply the dominant horizontal line within the region of detection. Therefore for each sub-image there are two sets of lines, one associated with the top of the image and one with the bottom, and each set consists of a screen overlap edge line and a candidate shadow line of the front screen overlap edge. These four lines are used in the subsequent analyses accordingly. As a byproduct of the line detection process, the transition magnitude across each line is computed, which is the average pixel value difference on the two sides of the line within a certain range.

Theoretically, the detected slopes of the fitting function for the front screen overlap edge in the front image and its shadow in the back image should be equal. However, they may differ by as much as several degrees in practice for several reasons, such as misalignment between the two phosphor screens during the x-ray exposure or screen positioning variations in the CR reader during the readout process The deviation represents the orientation misalignment between the front and back images. This misalignment must be corrected if its magnitude exceeds a level such that the reliability of the whole detection algorithm is impacted, especially in the calculation of the correlation functions between consecutive sub-image pairs.

Misalignment correction is accomplished by rotating either the front or the back image. If the front image is to be rotated, the rotation angle is $\theta = a\tan(k) - a\tan(k_f)$, where $k_f$ and $k$ are slopes of the fitting function for the front screen overlap edge in the front image and its shadow in the back image, respectively. If the back image is to be rotated, the angle is $\theta = a\tan(k_f) - a\tan(k)$, or if both images are to be rotated, the angle is $-a\tan(k_f)$ and $a\tan(k)$ respectively for the front and back images.

The screen overlap region in the back image is located between the back screen overlap edge and the shadow of the front screen overlap edge, based on which it is extracted for further analysis. The overlap region in the front image starts from the front screen overlap edge and is of the same size as that of the overlap region in the back image, based on which this region is extracted too.

A compensation factor can be applied to the size of the overlap region when the CR reader does not read beyond the screen edge. For example, element 320 in FIG. 3A shows the CR reader misses m lines of image pixels from the phosphor edge. The overlap region will therefore be m lines smaller, and a compensation can be made accordingly. This only works if the variability in screen orientation is very small during the CR scanning process.

Next, a plurality of measurements are conducted on every consecutive sub-image pair of each hypothesis and the hypothesis is deleted from the list if any measurement result is out of range. These measurements include the size of the overlap region, the average pixel intensity difference between the overlap regions in the front and back images, the overall transition magnitude of the shadow of front screen overlap edge in the back image, or the overall transition magnitude of the dominant horizontal line in the front image, etc.

The size of the overlap region should be within a fixed minimum and maximum range, which are determined by the cassette or screen holder fixture by design. For example, a loosely defined range of 100 to 300 pixel lines are used for an typical overlap size of 200 pixel lines.

Figure 9:
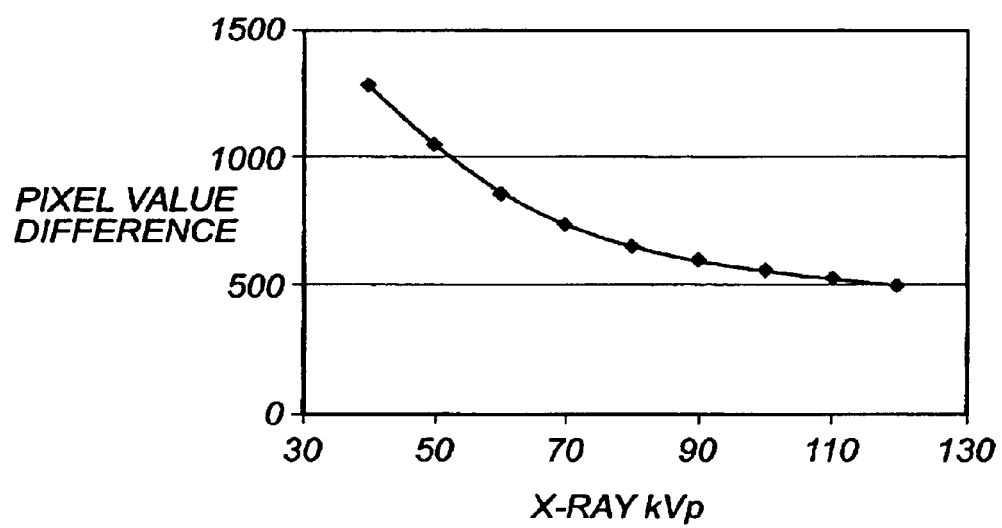
FIG. 9 shows the screen attenuation level as a function of x-ray beam energy.

The overlap region in the back image suffers an attenuation by the front screen. FIG. 9 shows the average pixel value difference at various x-ray beam energy (kVp). This data set are based on Kodak phosphor screens, which have a lead foil attached to the back of each phosphor for scatter reduction. This figure indicates that the pixel value in the overlap region of the front screen is higher than that in the back screen, but the difference should be within a certain range, which is a function of the x-ray beam energy. FIG. 9 is of particular interest to the maximum difference, because the average incident x-ray beam energy tends to be pushed toward the higher end by the imaging object due to beam hardening effect, which reduces the pixel value difference.

The pixel value difference in the overlap regions between each consecutive sub-image pair can be examined both globally and locally for improved computational efficiency. To conduct a global check, the overall average pixel value in the overlap region is computed separately for the front image and the back image. Typically 70–90 kVp of x-ray is used for full spine and full leg exams, and the corresponding pixel value difference is around 590–750 code values based on FIG. 9. A maximum value of 1000 is therefore selected for the average pixel value difference. In addition, a minimum value of 40 KVP is used to ensure that the average pixel value in the overlap region of the front image is higher than that in the back image. Both the minimum and the maximum values are loosely defined in order to factor in the beam energy variability and not to reject a valid hypothesis prematurely.

The average pixel value in the overlap region is also computed locally to improve the examination specificity. To each consecutive sub-image pair, the overlap regions in the front and the back images are partitioned into the same number of smaller regions, such as 8, and the average pixel value in each small partition is calculated and compared correspondingly. A maximum value of 1000 is selected for the similar reason to the global average pixel value difference examination. Because there may be some horizontal displacement between the recorded image information in the overlap regions, without knowing the exact displacement magnitude the local average pixel value comparison may run into the risk of comparing different image contents. To overcome this, the size of the local region should be sufficiently larger (e.g., 4 time) than the maximum horizontal displacements, which ensures that the image content mismatch between the corresponding local partitions are relatively small. Further, the allowable range chosen for the local average pixel value differences should be broader at the lower end, such as −100.

After the hypothesis list undergoes the size of overlap region check and the average pixel value difference check in the overlap region, a significant amount of false hypotheses are eliminated from the list and the rest will be passed down to the subsequent analyses.

A check of the overall transition magnitude of the shadow of the front screen overlap edge in the back image is conducted for each consecutive sub-image pair of each hypothesis left in the list. This examination is to exclude those hypotheses in which some sub-images acquired from the front phosphor screens are treated as back images. Because the shadow line is expected to be introduced by the front screen overlap edge, as shown in FIG. 9 the minimal transition magnitude should be larger than a minimum threshold.

A check of the overall transition magnitude of the dominant horizontal line in the front image is also conducted for each consecutive sub-image pair of each hypothesis left in the list. Because the front image does not undergo the same attenuation as the back image in the overlap region, and the image features in the front image should generally be continuous, the overall transition magnitude of the dominant horizontal line should not exceed a certain maximum value.

It should be noted that the whole detection process can finish if there is only one hypothesis left in the list at the end of any of the aforementioned checking processes. In this case, the last hypothesis contains the most likely arrangement of the sub-images for stitching.

Calculating the correlation function between consecutive sub-images is the most computational intensive step in the whole detection process. It is therefore arranged in the last few processing steps. The image content recorded in the overlap regions between each consecutive sub-image pair are the same except for some horizontal displacement, y_offset, between the corresponding pixels. This property is best characterized by the correlation function because it maximizes itself at the place where two overlap regions match the best, ie., the y_offset point. The correlation function only needs to be calculated in the horizontal direction because the two overlap regions only displaces in this direction. The function is computed using the formula given by $$c(\Delta) = \Sigma_{ij} F(x_i, y_j) \times B(x_i, y_j + \Delta),$$

where $F(x_i, y_j)$ and $B(x_i, y_j)$ is the pixel value at $(x_i, y_j)$ in the extracted overlap region from the front and back images, respectively, and $\Delta$ is the horizontal displacement parameter for correlation.

In a preferred embodiment of this invention, the normalized correlation function is computed using the formula given by $$c(\Delta)=[\Sigma_{ij}F(x_i, y_j) \times B(x_i, y_j+\Delta)]/[\Sigma_{ij}F(x_i, y_j)^2 \Sigma_{ij}B(x_i, y_j)^2]^{0.5}$$

This is because the normalized correlation function is independent of the image pixel value magnitude therefore is more suitable for comparison.

In a preferred embodiment of the present invention, the correlation function is calculated using the Fourier method.

Figure 7:
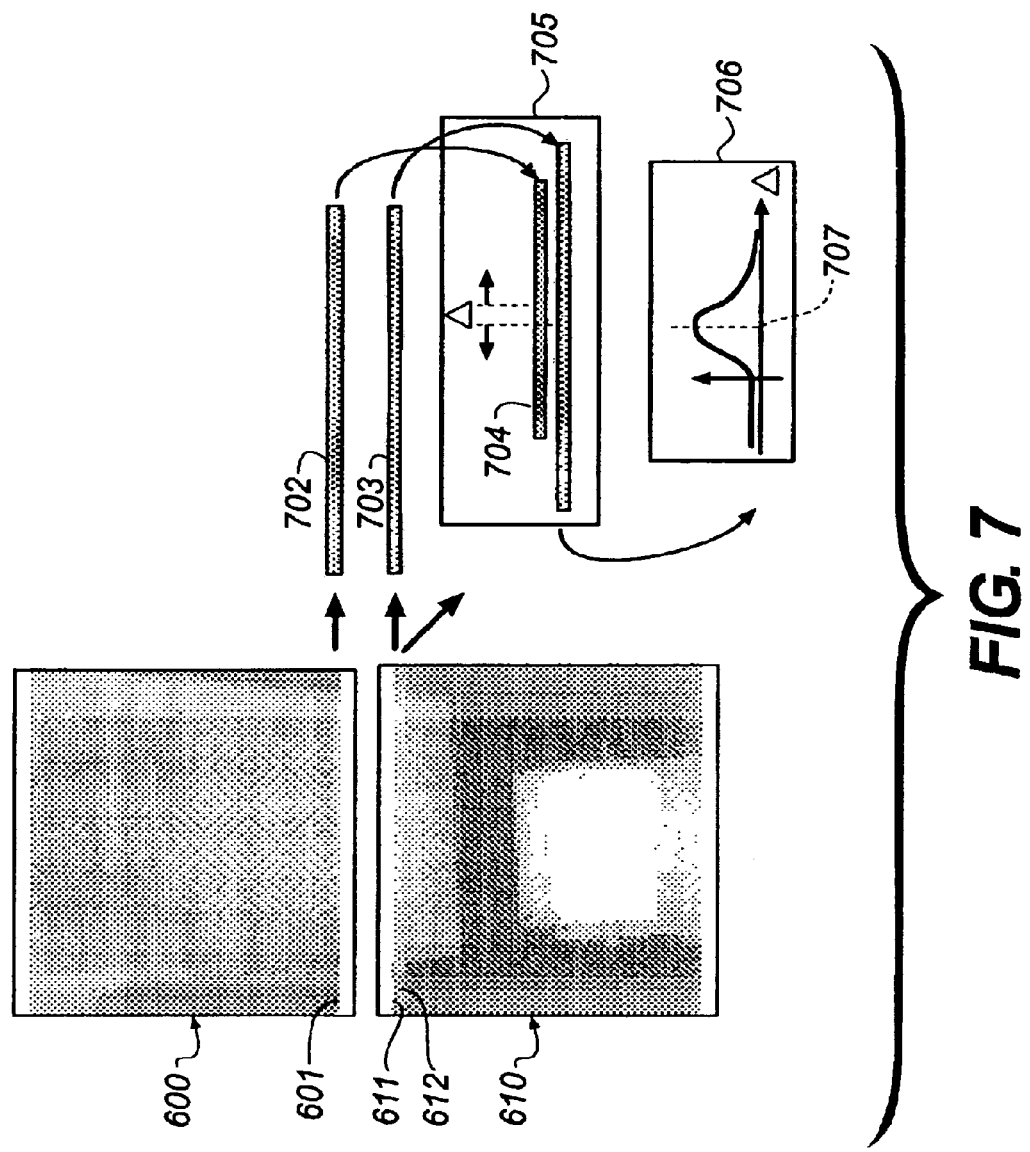
FIG. 7 is a diagrammatic view illustrating the major image processing steps that are used for calculating the correlation function for the overlap regions between a consecutive sub-image pair.

FIG. 7 describes the preferred implementation of this operation. First, the overlap region 702 and 703 are extracted from the front and back images respectively. Second, element 704 is obtained by extracting a portion of 702, then is correlated with 703 to create the correlation function $c(\Delta)$, 706. Similar results can be achieved by correlating a portion of 703 with 702. Third, the function maximum $c_{max}$ is detected and the corresponding value of $\Delta$ is identified as y_offset, 707.

Because the edge information in 702 and 703, including skin line, tissue boundaries, bone edges, collimation boundaries (element 304 in FIG. 3A), and hardware labels etc., contribute the most useful information to the correlation, in a preferred embodiment of the present invention, the low frequency content is removed from 702 and 703 in order to improve the correlation robustness. It has been found that the presence of the collimation shadow (element 304) helps improve the algorithm robustness in finding y_offset. Therefore, it is recommended to use collimation during the x-ray exposure.

Normally the correlation function is smooth, but if a stationary grid is used during the x-ray exposure, it imposes a periodic line pattern artifact in the acquired images. This artifact is particularly dominant when the grid is orientated in the vertical direction, and can correlate with itself, causing periodic small spikes to be introduced on top of the background correlation function. This artifact will negatively impact the accuracy in determining the location of the true function maximum. To address this issue, low-pass filtering of the correlation function is used before searching for the maximum.

The y_offset should be within a certain range because it indicates how much the horizontal displacement is between two consecutive sub-images. This range is determined by the hardware fixture that holds the cassettes/screens. A check of the y_offset value is therefore conducted and the corresponding hypothesis is rejected if y_offset is beyond a maximum allowable range, such as +/−70 pixels.

A special situation is that $c(\Delta)$ is constant, which means the overlap regions of two consecutive sub-images do not correlate. The corresponding hypothesis is rejected.

Finally, a figure-of-merit function is build for each hypothesis and the one with the highest score is selected as the most likely candidate for the whole detection process. All the aforementioned processes works on the local level of individual hypothesis, only this stage works on the global level that tries to compare all the possible hypotheses. In one embodiment of this invention, the figure-of-merit function of a hypothesis is build upon the sum of the maxima of the normalized correlation functions of all consecutive sub-image pairs, in particular:

$$\text{figure-of-merit}=\Sigma_k c_{max\_k},$$

where $c_{max\_k}$ is the maximum of the normalized correlation function of the kth consecutive sub-image pair in the hypothesis. By taking the sum of all the maxima, small error or bias in the calculated maximum of individual sub-image pair can be minimized.

Based on the detected hypothesis, the sub-images are rotated 180° if necessary, rearranged in order, then stitched together accordingly.

It will be understood that the invention would also be applicable to digital images resulting from overlapping conventional radiographic film images that have been digitized.

The invention has been described in detail with particular reference to certain preferred embodiments thereof, but it will be understood that variations and modifications can be effected within the spirit and scope of the invention.

Parts List 10 storage phosphor cassette
12 elongated rectangular shell
14 first open end
16 second open end
18 first phosphor plate assembly
20 second phosphor plate assembly
22,24 storage phosphor plate
26,28 latching assembly
29 central region
30,32 upper and lower members
34,36 side extrusions
40,42 inner surfaces
44,46 deflectors
101 cassettes
102 phosphor screens
103 elongated cassette
201 x-ray source
202 x-ray beam coverage
203 object/patient for imaging
204 x-ray antiscatter grid
205 a plurality of storage phosphor screens/cassettes for image capture
301 image 1 acquired with screen 1
302 image 2 acquired with screen 2, which is closer to the x-ray source than screen 1 and screen 3
303 image 3 acquired with screen 3
304 boundaries between collimated/no-collimated image regions
305 top edge shadow of screen 2 in image 3
306 bottom edge shadow of screen 2 in image 3
307 screen 1 and screen 2 overlap region in image 1
308 screen 2 and screen 3 overlap region in image 3
310 image 2 that is obtained with CR overscan
311 screen 2 top edge in overscanned image
312 screen 2 bottom edge in overscanned image
320 m lines of image pixels missed from the phosphor screen edge due to limitation in CR reader
401 x-ray source
402 front screen—lateral view
403 back screen—lateral view
404 front screen—front view
405 back screen—front view
406 back screen overlap edge
407 front screen overlap edge
501 elongated object
502 sub-image
503 overlap
504 hypothesis
505 reject hypothesis based on a plurality of measurements on each consecutive sub-image pair
506 calculate correlation function of each consecutive sub-image pair 507 reject hypothesis based on y_offset
508 compute figure-of-merit of each hypothesis
509 select hypothesis of maximum figure-of-merit for best candidate
510 process sub-images based on selected hypothesis for stitching
600 acquired front image
601 front screen overlap edge
602 extracted narrow band at the end of front image for identifying screen overlap edge
603 candidate edge transition pixels (falling slope) in 602
604 fitted line overlaid on top of candidate edge transition pixels
610 acquired back image
611 back screen overlap edge
612 shadow of front screen overlap edge in the back image
614 extracted narrow band at the beginning of back image for identifying screen overlap edge
615 candidate edge transition pixels (rising slope) in 614
616 fitted line overlaid on top of candidate edge transition pixels
622 extracted narrow band for searching of shadow of front screen overlap edge
623 candidate edge transition pixels (rising edge) in 622
624 fitted line overlaid on top of candidate edge transition pixels
702 extract screen overlap region from front image
703 extracted screen overlap region from back image
704 a portion of 702
705 process for conducting image correlation
706 correlation function
707 the location of maximum in the correlation function

What is claimed is:

1. A method for automatic arrangement determination of partial radiation images for reconstructing a stitched full image comprising:

acquiring at least two radiation sub-images of an elongated object by means of corresponding overlapped radiation recording media;

converting said recorded sub-images to digital images and storing them;

constructing a hypothesis list that includes all possible yet unique arrangements of sub-image order, orientation and overlap;

detecting overlap regions for each consecutive sub-images pair in each hypothesis;

conducting a plurality of different measurements on every consecutive sub-image pair of each hypothesis and deleting the hypothesis from the list if any measurement result is out of range;

calculating the correlation function of the overlap regions for each consecutive sub-image pair in each hypothesis left in said hypothesis list and finding the function maximum and the horizontal displacement between the sub-image pair;

checking the magnitude of the horizontal displacement between each consecutive sub-image pair and rejecting the hypothesis from the hypothesis list if the magnitude is out of range;

establishing an overall figure-of-merit for each hypothesis left in the hypothesis list based on the sum of the maximum of the correlation functions;

selecting the hypothesis of maximum figure-of-merit for best candidate; and processing the sub-images based on selected hypothesis for stitching to produce an output image consisting of the stitched sub-images.

2. The method of claim 1 wherein in said acquiring, said elongated object is a human body part including one of a spine or a leg of an individual.

3. The method of claim 1 wherein said acquiring is effected by overlapping storage phosphor screens and said converting is carried out by a storage phosphor CR reader which produces digital sub-images which are stored in digital memory.

4. The method of claim 1 wherein said constructing, detecting, conducting, calculating, checking, establishing, selecting and processing are carried out by a digital processor.

5. The method of claim 1 wherein said output image is utilized by an output device to display the output image on a monitor and/or to produce a hard copy of the output image.

6. The method of claim 1 wherein said detecting overlap regions includes locating the screen overlap edges from the front and back images of a consecutive sub-image pair; and detecting the shadow of the front screen overlap edge in the back image.

7. The method of claim 6 wherein said locating the screen overlap edges includes:

computing all of the significant edge transition pixels in the proximity of the screen overlap edge; and performing line delineation of the candidate pixels of the screen overlap edge.

8. The method of claim 6 wherein said locating the screen overlap edge includes:

extracting a narrow hand from the end of the front image;

computing a one dimensional derivative of the image in the vertical direction; and fitting a linear function to the candidate edge pixels and obtaining the best fitting parameters when the least square error is reached.

9. The method of claim 8 including comparing the screen overlap edge found in the front image with its shadow in the back image for image registration.

10. The method of claim 8 wherein said one dimensional derivative is one of [−1,0,1], [−1,0,0,0,1], [−1,0,0,0,0, 1].

11. The method of claim 1 wherein said conducting of said different measurements includes one or more of the following measurements, size of the overlap region, average pixel intensity difference between the overlap regions in the front and back regions, the overall transition magnitude of the shadow of front screen overlap edge in the back image, and the overall transition magnitude of the dominant horizontal line in the front image.

12. The method of claim 1 wherein said correlation function is computed using the following formula:

$$c(\Delta)=\Sigma_{ij}F(x_i, y_j) \times B(x_i, y_j+\Delta),$$

where $F(x_i, y_j)$ and $B(x_i, y_j)$ is the pixel value at $(x_i, y_j)$ in the extracted overlap region from the front and back images, respectively, and $\Delta$ is the horizontal displacement parameter for correlation.

13. The method of claim 1 wherein said correlation function is computed using the formula:

$$c(\Delta)=[\Sigma_{ij}F(x_i, y_j) \times B(x_i, y_j+\Delta)]/[\Sigma_{ij}F(x_i, y_j)^2 \Sigma_{ij}B(x_i, y_j)^2]^{0.5}$$

where $F(x_i, y_j)$ and $B(x_i, y_j)$ is the pixel value at $(x_i, y_j)$ in the extracted overlap region from the front and back images, respectively, and $\Delta$ is the horizontal displacement parameter for correlation.

14. The method of claim 1 wherein said correlation function is calculated using a Fourier transform method.

15. The method of claim 1 wherein said calculating the correlation function includes removing the low frequency content to improve correlation robustness.

16. The method of claim 1 wherein said establishing an overall figure of merit is calculated by the following formula:

$$\text{figure-of-merit} = \Sigma_k c_{max\_k},$$

where $c_{max\_k}$ is the maximum of the normalized correlation function of the kth of the kth consecutive sub-image pair in the hypothesis.

17. The method of claim 1 wherein said acquiring is effected by overlapping film media and said converting is carried out by a film digitizer which produces digital sub-images which are stored in digital memory.

* * * * *